12

United States Patent [19]
Angelastro et al.

[11] Patent Number: 5,102,915
[45] Date of Patent: Apr. 7, 1992

[54] CYCLOPROPYL SQUALENE DERIVATIVES AND THEIR USE AS INHIBITORS OF CHOLESTEROL SYNTHESIS

[75] Inventors: Michael R. Angelastro, Loveland; Norton P. Peet; Philippe Bey, both of Cincinnati, all of Ohio

[73] Assignee: Merrell Dow Pharmaceuticals Inc., Cincinnati, Ohio

[21] Appl. No.: 722,777

[22] Filed: Jun. 28, 1991

Related U.S. Application Data

[62] Division of Ser. No. 497,477, Mar. 22, 1990, Pat. No. 5,051,534.

[51] Int. Cl.$^5$ ............................................. A61K 31/075
[52] U.S. Cl. .................................. 514/715; 514/824
[58] Field of Search ................................. 514/715, 824

[56] References Cited

U.S. PATENT DOCUMENTS 2,330,979  10/1943  Krantz et al. ........................ 568/579
4,891,367   1/1990  Angelastro et al. ................. 514/178

OTHER PUBLICATIONS

Sen et al., J. Am. Chem. Soc. 111, 1508–1510 (1989).
Taylor et al., J. Biol. Chem. 261(320, 15039–44 (1986).
Cattel et al., Lipids 21(1), 31–38 (1986).

Primary Examiner—Frederick E. Waddell
Assistant Examiner—Kimberly R. Jordan
Attorney, Agent, or Firm—Michael J. Sayles

[57] ABSTRACT

The present invention relates to a group of compounds which are novel squalene derivatives containing the cyclopropyloxy functionality and which act to inhibit the synthesis of cholesterol in mammals and in fungi.

1 Claim, No Drawings

CYCLOPROPYL SQUALENE DERIVATIVES AND THEIR USE AS INHIBITORS OF CHOLESTEROL SYNTHESIS

This is a divisional of application Ser. No. 497,477, filed Mar. 22, 1990, now U.S. Pat. No. 5,051,534.

FIELD OF INVENTION

The present invention relates to a group of compounds which are novel squalene derivatives containing the cyclopropyloxy functionality and which act to inhibit the synthesis of cholesterol in mammals and in fungi.

BACKGROUND OF INVENTION

Vascular disease, because of its effects upon the brain, heart, kidneys, extremities, and other vital organs, is a leading cause of morbidity and mortality in the U.S. and in most Western countries. In this regard, much has been learned about atherosclerosis, and the lipidemias, with particular reference to cholesterol. In particular, there is convincing evidence of a reciprocal relationship between a high serum cholesterol and the incidence of atherosclerosis and its complications. Much interest has been expressed in recent years in reducing the level of serum cholesterol. However, some studies have shown that even radical reductions in dietary cholesterol achieves a modest decrease of only 10 to 15% in plasma cholesterol. Thus, it has been appreciated that further reductions in serum cholesterol will require other therapeutic measures, including the inhibition of cholesterol synthesis in the body.

The enzymatic biosynthesis of cholesterol is a complex process which requires altogether some 25 reaction steps. The pathway can be divided into three stages: (1) the conversion of acetic acid to mevalonic acid; (2) the conversion of mevalonic acid into squalene; and, (3) the conversion of squalene into cholesterol. In the last stage of cholesterol biosynthesis, squalene is converted to squalene 2,3-epoxide via oxidation, a reaction catalyzed by squalene monooxygenase, also known as squalene epoxidase. The squalene 2,3-epoxide then undergoes cyclization to lanosterol, the first sterol to be formed; the cyclization of 2,3-oxidosqualene to lanosterol is catalyzed by the microsomal enzyme 2,3-oxidosqualene lanosterol-cyclase (squalene cyclase). Inhibition of either squalene epoxidase or squalene cyclase would result in the inhibition of cholesterol synthesis in animals. (See generally, Taylor, Frederick R., Kandutsch, Andrew A., Gayen, Apurba K., Nelson, James A., Nelson, Sharon S., Phirwa, Seloka, and Spencer, Thomas A. 24,25-Epoxysterol Metabolism in Cultured Mammalian Cells and Repression of 3-Hydroxy-3-methylglutaryl-CoA Reductase, *The Journal of Biological Chemistry*, 261, 15039–15044 (1986), incorporated herein by reference.)

In addition, it has recently been reported that certain compounds, such as allylamines, act as inhibitors of squalene epoxidase and have potent antifungal activity. (See generally, Stutz, Anton, Allylamine Derivatives-A New Class of Active Substances in Antifungal Chemotherapy, *Angew. Chem. Int. Ed. Engl.*, 26, 320–328 (1987)). Fungal infections (mycoses) are found throughout the world. Only a few structural classes of compounds currently satisfy the demands of modern chemotherapy in their treatment and the search for new types of active substances is of major therapeutic importance.

As inhibitors of squalene epoxidase in animals, the compounds of the present invention are believed to be useful in the treatment of fungal infections through the inhibition o cholesterol biosynthesis.

SUMMARY OF THE INVENTION

The present invention relates to compounds according to Formula I below:

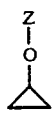   FORMULA I wherein Z is selected from the group consisting of A, B, C, and D below:

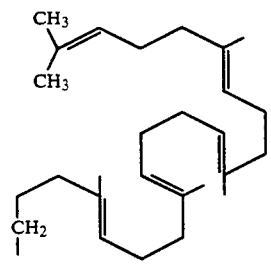   A

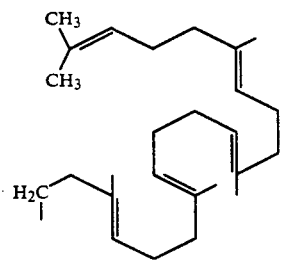   B

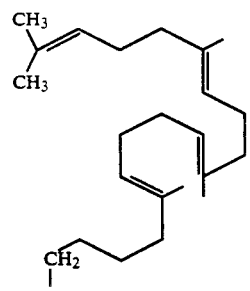   C

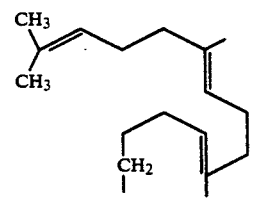   D wherein all unsaturated bonds are trans.

DETAILED DESCRIPTION OF THE INVENTION

Compounds according to the invention can be made according to Reaction Scheme I.

REACTION SCHEME I

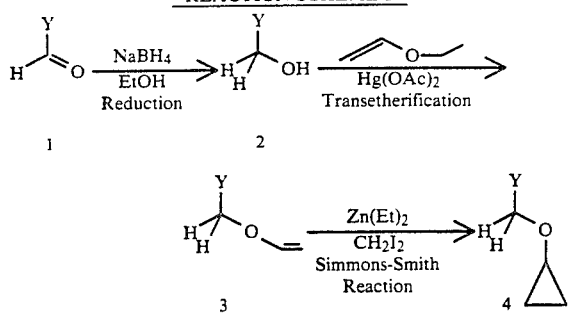

wherein Y is selected from the group consisting of:

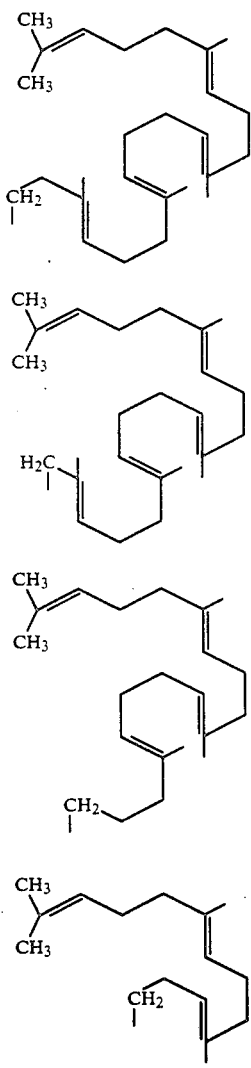

It will be understood that Y is Z minus one methylene group and that the double bonds shown in the carbon chain in the formulae above and below and in all the compounds disclosed in this application are trans.

An appropriate aldehyde is selected from the group consisting of 4,8,13,17,21-pentamethyl-4,8,12,16,20-docosapentaenal, 3,7,12,16,20-pentamethyl-3,7,11,15,19-heneicosapentaenal (tetranorsqualene aldehyde), 5,10,14,18-tetramethyl-5,9,13,17-nonadedcatetraenal, or 5,9,13-trimethyl-4,8,12-tetradecatrienal. It will be seen that the choice of the starting aldehyde will determine which of the final compounds according to Formula I is made. The above aldehydes are all known in the art. (See, (1) Sen, S. E.; Prestwick, G. D., *J. Am. Soc.*, 111, 1508-10 (1989) and Sen, S. W.; Prestwick, G.D., *J. Med. Chem.*, 32, 2152-58 (1989) for 4,8,13,17,21-pentamethyl-4,8,12,16,20-docosapentaenal (trisnorsqualene aldehyde); (2) van Tamelen, E.E.; Pedlar, A.D.; Li, E.; James, D.R., *J. Amer. Chem. Soc.*, 99, 6778-80 (1977) for 3,7,12,16,20-pentamethyl-3,7,11,15,19-heneicosapentaenal (tetranorsqualene aldehyde); (3) Herin, M.; Delbar, P.; Remion, J.; Sandra, P.; and Krief, A.; Synthesis of Squalene Epoxidase and Lanosterol Analogues for a Biosynthetic Experiment, *Tetrahedron Letters*, 33, 3107-3110, and Corey, E. J.; Krief, A.; and Yamamoto, H., Conversion of Des-6-methyl-2,3-oxidosqualene to 19-Norlanosterol by 2,3-oxidosqualene-Sterol Cyclase, *J. Amer. Chem. Soc.*, 93, 1493 (1971) for 5,10,14,18-tetramethyl-5,9,13,17-nonadecatetraenal; and, (4) Coates, R. M.; Ley, D. A.; and Cavender, P. I.; Synthesis and Carbon-13 Nuclear Magnetic Resonance Spectra of all-trans-Geranylgeraniol and its Nor Analogues, *J. Org. Chem.*, 43(26), 4915 (1978) for 5,9,13-trimethyl-4,8,12-tetradecatrienal all incorporated herein by reference.)

The aldehyde 1 is chosen such that Y has the same definition as that desired in the final product. The aldehyde 1 is first reduced to the corresponding alcohol 2 by a reducing agent such as sodium borohydride. The aldehyde 1 is first dissolved in ethanol, for example, and sodium borohydride is added in approximately an equimolar amount and the solution stirred at room temperature under argon gas, for example. The reaction may be quenched with acetic acid (1%, for example). The above product can be extracted and purified by techniques well-known in the art. The reaction is poured into ethyl acetate/water, the layers separated, and the ethyl acetate layer washed with sodium bicarbonate and brine. The organic extract is dried over magnesium sulfate, the solvent removed and the crude material is purified by flash chromatography to give the desired product.

The above alcohol 2 is then reacted with ethyl vinyl ether in the presence of a catalytic amount of mercury diacetate to form the corresponding vinyl ether 3. The reaction mixture is allowed to reflux for several hours, then cooled, poured into water and extracted with ether. The ether extracts are washed and dried over magnesium sulfate, yielding a crude material which can be purified by flash chromatography, for example, to give the desired vinyl ether.

The vinyl ether product 3 is then reacted with equimolar amounts of diiodomethane (in ether) and diethyl zinc to form the corresponding cyclopropyl ether 4 in a procedure known as the Simmons-Smith cyclopropanation. (See, March, J., *Advanced Organic Chemistry*, 3rd Ed., John Wiley and Sons, Inc. (1985); Simmons, Cairns, Vladochich and Hoiness, *Org. React.* 20, 1-131 (1973) and Furukawa; and Kowabata, *Adv. Organomet. Chem.*, 12, 83-134 (pp. 84-103) (1974) all incorporated herein by reference.) The diiodomethane (in ether) is preferably added dropwise, in an approximately equimolar amount, to the solution of substrate and an equimolar amount of diethyl zinc in ether. After stirring for several hours, the reaction mixture is quenched with saturated ammonium chloride, for example, and extracted with ether. The ether layer is separated and washed with brine and dried over magnesium sulfate. Removal of the ether in vacuo yields a crude product, which can be further purified by techniques well-known in the art to yield the desired cyclopropyl ether.

Examples of compounds of the present invention which can be made according to the processes described above are the following:

4,8,13,17,21-Pentamethyl-4,8,12,16,20-docosapentaenyl-1-olcyclopropyl ether (Z=A).

3,7,12,16,20-Pentamethyl-3,7,11,15,19-heneicosapentaen-1-olcyclopropyl ether (Z=B).

5,10,14,18-Tetramethyl-5,9,13,17-nonadecatetraen-1-olcyclopropyl ether (Z=C).

5,9,13-Trimethyl-4,8,12-tetradecatrien-1-olcyclopropyl ether (Z=D).

The following assay is used to test compounds for their ability to inhibit 2,3-oxidosqualene lanosterol-cyclase (squalene cyclase) or squalene epoxidase. Microsomes, prepared by ultracentrifugation of homogenates of rat liver, are incubated at 37° C for 45 minutes in the presence of 60 $\mu$M $^3$H-squalene, 2.0 mM NADPH, 0.01 mM FAD, and the high speed supernatant fraction from the microsomal preparation. Blanks, in which NADPH has been omitted, are run simultaneously with the test compounds. Compounds are tested at concentrations of >0.0 to 100.0 $\mu$M.

METHOD 1

Following incubation the samples are saponified, standards are added to each sample, and then the reaction products are extracted into hexane. The hexane extracts are dried and then the dried extracts are redissolved in chloroform. The reaction products contained in the extracts are then separated by thin layer chromatography (TLC). Spots containing the reaction products are scraped from the TLC plates and counted for radioactivity in a scintillation counter. An $IC_{50}$ is finally calculated.

METHOD 2

Incubation reactions are stopped by the addition of chloroform:methanol, standards are added and the reaction products and standards are extracted into chloroform. The chloroform extracts are dried, and the residue is dissolved in toluene:methanol. The reaction products and standards contained in the dissolved residue are separated by high performance liquid chromatography (HPLC). Chromatographic peaks containing reaction products are monitored for radioactivity with a flow-through scintillation counter connected in series with the HPLC column. An $IC_{50}$ (Inhibitory Concentration) is calculated based on the radioactivity in controls and samples.

The following illustrates inhibition of squalene expoxidase for some of the compounds of the present invention according to the above procedures:

| Compound Name | $IC_{50}$ Value |
|---|---|
| 1. 4,8,13,17,21-Pentamethyl-4,8,12,16,20-docosapentaenyl-1-ol cyclopropyl ether | 42 $\mu$M |

The above data provide evidence that the disclosed compounds inhibit squalene epoxidase and that the compounds of claim 1 are therefore useful in both methods to inhibit cholesterol synthesis and methods of treating fungal infections.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 $\mu$g or less to 500 mg or more of the active compound per mg or ml of carrier.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as Remington's Pharmaceutical Manufacturing, 13 Ed., Mack Publishing Co., Easton, Pennsylvania (1965).

The compounds of this invention may also be utilized in research and diagnostics or as analytical references or standards, and the like. The compounds may be incorporated into any inert carrier so that they may be utilized in routine serum assays, blood levels, urine levels, etc., according to techniques well known in the art. Therefore, are comprised of an inert carrier and a compound of Formula I, or a salt thereof. An inert carrier is any material which does not interreact with the compound to be carried and which lends support, means of conveyance, bulk, traceable material, and the like to the compound to be carried. The amount of compound used in such compositions is that amount which produces the desired result or exerts a desired influence on the particular procedure being performed.

The preferred route of administration is oral administration. For oral administration the compounds can be formulated by those skilled in the art into solid or liquid compositions such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance patient acceptance of the tablets. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable compositions of the active compound in a physiologically acceptable diluent with a pharmaceutical carrier. Those skilled in the art will be able to readily prepare such compositions using sterile liquids or a mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-l,3-dioxolane-4-methanol; ethers such as poly(ethyleneglycol) 400, oils, fatty acids, fatty acid esters or glycerides, or acetylated fatty acid glycerides with or without the addition of pharmaceutically acceptable surfactants such as a soap or a detergent; suspending agents such as pectin, carbomers, methylcellulose, hydroxypropylmethylcellulose, or carboxymethylcellulose; or emulsifying agents and other pharmaceutically adjuvants.

Illustrative of oils which can be used in parenteral formulations are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, and alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkylbeta-aminopropionates, and 2-alkylimidazoline quarternary ammonium salts, as well as mixtures.

The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a nonionic surfactant having a hydrophilelipophile balance (HLB) of from about 12 to about 17. The quantity of surfactant in such formulations range from about to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan mono-oleate and the high molecular weight adducts of ethylene oxide with a hydrophobic base, formed by the condensation of propylene oxide with propylene glycol.

The exact amount of the compound or compounds to be employed in the compositions of the present invention, i.e., the amount of the subject compound or compounds sufficient to provide the desired effect, depends on various factors such as the compound employed; type of administration; the size, age and species of animal; the route, time and frequency of administration; and, the physiological effect desired. The amount of active compound to be administered can be ascertained by conventional range finding techniques known to skilled clinicians.

The following examples are presented to illustrate the present invention but they should not be construed as limiting the same in any way.

EXAMPLE 1

Preparation of 4,8,13,17,21-Pentamethyl-4,8,12,16,20-Docosapentaenyl-1-ol Cyclopropyl Ether First, the aldehyde 4,8,13,17,21-pentamethyl-4,8,12,16,20-docosapentaenal (8.0 g, 20.8 mmol) was dissolved in 200 ml ethanol. Sodium borohydride (0.789 g, 20.8 mmol) was added and the solution stirred for 15 minutes at room temperature under argon. The reaction was quenched with 1% acetic acid and then poured into 400 ml ethyl acetate. The layers were separated and the ethyl acetate layer washed with sodium bicarbonate (2×150 ml), brine (2×150 ml), and dried over magnesium sulfate. The solvent was removed in vacuo and the crude material purified by flash chromatography to give 5.1 g of 4,8,13,17,21-pentamethyl-4,8,12,16,20-docosapentaen-1-ol.

Mercury diacetate (0.33 g, 1.03 mmol) was added to a solution of 4,8,13,17,21-pentamethyl-4,8,12,16,20-docosapentaen-1-ol (2.00 g, 5.17 mmol) in 50 ml of ethyl and the reaction refluxed overnight. The reaction was poured into 350 ml of water and extracted with ether. The ether extracts were washed with brine and dried over magnesium sulfate. Removal of the ether in vacuo gave the crude material which was purified by flash chromatography using 95/5 (hexane/ethyl acetate), to give 1.69 g of 4,8,13,17,21-pentamethyl-4,8,11,16,20-docosapentaen-1-ol vinyl ether.

Diethyl zinc (0.606 ml, 1.0 M in hexane) was added to 4,8,13,17,21-pentamethyl-4,8,12,16,20-docosapentaen-1-ol vinyl ether (0.250 g, 0.606 mmol) in 6 ml ether under argon. Diiodomethane (0.240 g, 0.606 mmol, 73.3 $\mu$l), in 2 ml ether, was added dropwise over 0.5 hour. After stirring overnight at room temperature, the reaction was quenched with saturated ammonium chloride. An additional 40 ml of ether and 20 ml of saturated ammonium chloride were added and the layers separated. The ether layer was washed with brine and dried over magnesium sulfate. Removal of the solvent in vacuo yielded 0.32 g of crude product, which was shown to be a 3:1 mixture by capillary gas chromatography of 4,8,13,17,21-pentamethyl-4,8,12,16,20-docosapentaen-1-ol cyclopropyl ether and a dicyclopropyl compound.

EXAMPLE 2

Preparation of 3,7,12,16,20-Pententamethyl-3,7,11,15,19-Heneicosapentaen-1ol Cyclopropyl Ether The alcohol 3,7,12,16,20-pentamethyl-3,7,11,15,19-heneicosapentaen-1-ol can be prepared directly from the aldehyde 3,7,12,16,20-pentamethyl-3,7,11,15,19-heneicosapentaenal (tetranorsqualene aldehyde), by following the procedure described in Example 1 above. First, the aldehyde is dissolved in ethanol and then an approximately equimolar amount of sodium borohydride is added and the reaction stirred at room temperature for a short period of time under an inert atmosphere. The reaction can be quenched with 1% acetic acid and then poured into ethyl acetate. The layers are separated and the ethyl acetate layer washed with sodium bicarbonate, brine, and dried over magnesium sulfate. The solvent is then removed in vacuo and the crude material can be purified by flash chromatography to give the desired product, 3,7,12,16,20-pentamethyl-3,7,11,15,19-heneicosapentaen-1-ol.

Mercury diacetate (0.33 g, 1.03 mmol) is added to a solution of 1.93 g of 3,7,12,16,20-pentamethyl-3,7,11,15,19-heneicosapentaen-1-ol (5.17 mmol) in 50 ml of ethyl vinyl ether and the reaction refluxed overnight. The reaction is poured into 350 ml of water and extracted with ether (2×200 ml). The ether extracts were washed with brine (2×150 ml) and dried over magnesium sulfate. Removal of the ether in vacuo gave the crude material which was purified by flash chromatography using 95/5 (hexane/ethyl acetate), to give the desired vinyl ether, 3,7,12,16,20-pentamethyl-3,7,11,15,19-heneicosapentaen-1-ol vinyl ether.

Diethyl zinc (0.606 ml, 1.0 M in hexane) is added to 0.242 g of 3,7,12,16,20-pentamethyl-3,7,11,15,19-heneicosapentaen-1-ol vinyl ether in 6 ml ether under Diiodomethane (0.606 mmol, 73.3 μl) in 2 ml ether, is added dropwise over 0.5 hour. After stirring overnight at room temperature, the reaction was quenched with saturated ammonium chloride. An additional 40 ml of ether and 20 ml of saturated ammonium chloride are added and the layers separated. The ether layer is washed with brine (2×30 ml) and dried over magnesium sulfate. Removal of the solvent in vacuo yields the desired product, 3,7,12,16,20-pentamethyl-3,7,11,15,19-heneicosapentaen-1-ol cyclopropyl ether, which is purified by chromatography.

What is claimed is:

1. A method of treating hypercholesterolemia in mammals in need thereof comprising administering to the mammal a therapeutically effective amount of a compound of the formula:

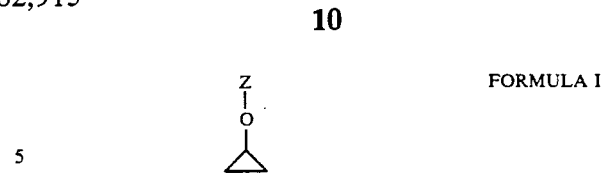

FORMULA I wherein Z is selected from the group consisting of Formula II, Formula III, Formula IV, and Formula V below:

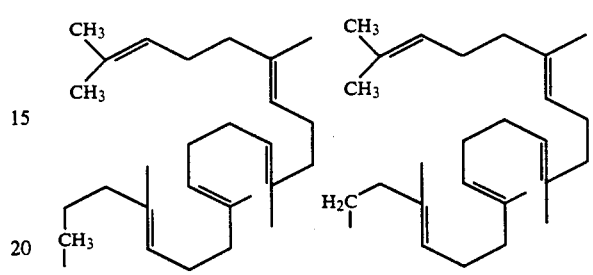

FORMULA II         FORMULA III

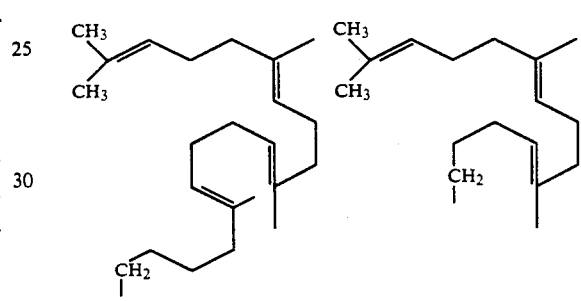

FORMULA IV         FORMULA V and wherein all unsaturated bonds are trans.

* * * * *